United States Patent [19]

Koshar

[11] 3,984,357
[45] Oct. 5, 1976

[54] FLUOROALIPHATICSULFONYL SUBSTITUTED ETHYLENES

[75] Inventor: Robert J. Koshar, Mahtomedi, Minn.

[73] Assignee: Minnesota Mining and Manufacturing Company, Saint Paul, Minn.

[22] Filed: Mar. 27, 1974

[21] Appl. No.: 455,141

Related U.S. Application Data

[62] Division of Ser. No. 300,754, Oct. 25, 1972, Pat. No. 3,932,526.

[52] U.S. Cl. .............................. 260/2 R; 526/204; 526/206; 260/2 N; 260/2 A; 260/345.1; 260/47 EN; 260/47 UA; 260/79.3 M; 260/583 EE; 260/583 GG; 260/592; 260/593 H; 260/329 S; 252/426; 260/326.5 SF; 260/346.1 R; 260/293.85; 260/347.2
[51] Int. Cl.² ................ C07C 147/04; B01J 31/02
[58] Field of Search ............... 260/583 EE, 583 GG, 260/592, 593 H, 47 EN, 2 N, 2; 252/426

[56] References Cited
UNITED STATES PATENTS

| | | | |
|---|---|---|---|
| 2,558,875 | 7/1951 | Pearson.................. | 260/583 GG X |
| 2,959,617 | 11/1960 | McKusick et al. ......... | 260/563 R X |
| 3,355,494 | 11/1967 | Lyness et al. ........... | 260/592 |
| 3,527,807 | 9/1970 | Tesoro et al. ............ | 260/583 EE X |
| 3,535,381 | 10/1970 | Hauptschein et al. ... | 260/583 GG X |
| 3,578,717 | 5/1971 | Mitsch et al. ............ | 260/583 EE |
| 3,632,843 | 1/1972 | Allen et al. ............... | 252/426 UX |

*Primary Examiner*—Allen B. Curtis
*Attorney, Agent, or Firm*—Alexander, Sell, Steldt and DeLaHunt

[57] ABSTRACT

Fluoroaliphaticsulfonyl substituted ethylenes, useful as catalysts in polymerization of monomers, e.g., epoxide, vinyl ether, and N-vinyl monomers, are prepared by condensation of precursor fluoroaliphaticsulfonyl methanes with aldehydes or N-formyl compounds.

9 Claims, No Drawings

FLUOROALIPHATICSULFONYL SUBSTITUTED ETHYLENES

This is a division of application Ser. No. 300,754 filed Oct. 25, 1972, now U.S. Pat. No. 3,932,526.

FIELD OF THE INVENTION

This invention relates to novel fluoroaliphaticsulfonyl substituted ethylene compounds, their use as catalysts, and to a method of their preparation. The invention also relates to novel precursor fluoroaliphaticsulfonyl methanes used in the method.

BACKGROUND OF THE PRIOR ART

The curing of epoxide, vinyl ether, and N-vinyl monomers in the presence of catalysts is well known in the art. For example, epoxides can be cured in the presence of boron trifluoride and complexes thereof and vinyl alkyl ethers can be polymerized in the presence of alluminum trichloride and related Lewis acids. While the use of such acid catalysts has been found to be advantageous in many cases, their use is often objectionable because many acid catalysts are highly corrosive to various substrates, such as metals. Other catalysts are objectionable because of their volatility. The present invention provides catalysts which are highly effective, substantially non-corrosive, and essentially non-volatile.

In one aspect, this invention provides a novel class of substituted ethylene compounds useful as catalysts for curing monomers. These ethylenes are non-acidic, therefore non-corrosive, and they are non-volatile during use. Some of the substituted ethylenes can be used in admixture with the monomers to provide latently curable compositions having a desirably long shelf or pot life.

In another aspect, the invention provides novel precursor methanes useful in preparing the substituted ethylenes of the invention.

Certain precursor methanes useful in the chemical reaction to obtain the novel fluoroaliphaticsulfonyl substituted ethylenes of the invention are known. Examples include bis(perfluoroalkylsulfonyl)methanes disclosed in a paper presented by H. A. Brown to the American Chemical Society in Minneapolis, Minnesota, in September 1955, bis(perfluoromethylsulfonyl)methane, disclosed in U.S. Pat. No. 2,732,398 and by Gramstad and Haszeldine in *Journal of Chemical Soc.*, 4069 (1957), and bis(perfluoroalkylsulfonyl)methanes, disclosed in U.S. Pat. No. 3,281,472. Likewise, somewhat related substituted ethylenes are known, e.g., bis(alkylsulfonyl) ethylenes and perfluoromethyl sulfonyl ethylenes see U.S. Pat. No. 3,335,188 and L. M. Yagupolski and A. G. Pateleimonov in *Zh. Obshch. Khim.*, 36, (3) 416 (1966), respectively, but these substituted ethylenes are considerably weaker than the substituted ethylenes of the invention, if at all effective, in catalyzing epoxide, vinyl ether, and N-vinyl monomer polymerization.

DESCRIPTION OF THE INVENTION

The novel fluoroaliphaticsulfonyl substituted ethylenes of the invention are formed by the chemical condensation of certain precursor fluoroaliphaticsulfonyl methanes with aldehydes or N-formyl compounds, i.e., compounds characterized by containing a "—CHO" group. The fluoroaliphatic sulfonyl substituted ethylenes of the invention are preferably represented by the general formula:

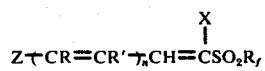

wherein $R_f$ is a monovalent saturated fluoroaliphatic radical, for example, containing from 1 to 18 carbon atoms (preferably 1 to 8 carbon atoms) with the majority of the carbon atoms preferably being perfluorinated; X is a monovalent, non-ionic, electron-withdrawing radical that is at least as electron-withdrawing as a benzoyl radical [i.e., having a Hammett sigma (para) value of at least 0.5], e.g., a cyano, arylcarbonyl, alkylcarbonyl, perfluoroalkylcarbonyl, arylsulfonyl, perfluoroalkylsulfonyl, nitro, fluorosulfonyl, or chlorosulfonyl group, (preferably X has the general formula $R'_fSO_2$ where $R'_f$ is a fluoroaliphatic group as defined for $R_f$ above, including $R'_f$ being identical to $R_f$); R is hydrogen, alkyl (preferably having 1–3 carbon atoms), or phenyl; R' is the same as R with at least one of R or R' being hydrogen; n is an integer from zero to 7 depending on Z; n is 1 to 7 when Z is hydrogen, alkyl, alkenyl, aryl, arylalkyl, alkylaryl or 2-furyl; n is zero when Z is aryl or arylmethyl (e.g., benzyl) or amino, dialkylamino, arylalkylamino, diarylamino, alkylamino, arylamino or heterocyclic nitrogen-containing organic radical having a free valence on a ring nitrogen atom (e.g., a morpholino group) or Z is an unsaturated, conjugated heterocyclic organic radical containing one or more oxygen, sulfur, or nitrogen heteroatom and having a free valence on a carbon atom (e.g.,

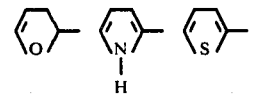

Additionally, Z may contain 1–3 substituent groups which can vary widely from highly electron-donating groups to highly electron-withdrawing groups, provided they are less reactive than the formyl group with the precursor methane. Exemplary substituents include groups such as halo (e.g., chloro, bromo, fluoro), cyano, hydroxy, nitro, lower alkyl (1–3 carbon atoms), lower perfluoroalkyl (1–3 carbon atoms), alkylcarbonyl, arylcarbonyl, alkoxycarbonyl, lower alkenyl, alkylsulfonyl, fluorosulfonyl, alkoxy, etc.

As mentioned above a majority of the carbon atoms of the fluoroaliphatic groups $R_f$ and $R'_f$ are perfluorinated. The term "perfluorinated" and the prefex "perfluoro" is employed to denote substitution of all carbon-bonded hydrogen atoms by fluorine atoms, in accord with the recognized usage of these terms, see U.S. Pat. No. 2,732,398. This usage carries no implication of similarities in properties between corresponding groups and compounds of hydrocarbon and fluorocarbon systems; hydrogen and fluorine are not chemically equivalent or similar.

The above-mentioned fluoroaliphatic groups can contain chlorine atoms bonded to the carbon atoms as well as having fluorine and hydrogen atoms bonded to carbon atom. Preferably for any two carbons bonded together in a chain, there is no more than one hydrogen atom or one chlorine atom, with fluorine atoms occupying the remaining non-skeletal carbon bonds.

The fluoroaliphatic radical may be a straight or branched chain, or a straight chain including a cyclic portion. Additionally, the fluoroaliphatic group may contain an oxygen atom linking two carbon atoms, e.g., $-CF_2OCF_2-$, or a nitrogen atom linking three carbon atoms, e.g., $(R_fCF_2)NCF_2-$. Exemplary fluoroaliphatic groups include perfluoromethyl, perfluorobutyl, perfluorooctyl, perfluorododecyl, perfluoroisopropyl, perfluoro(2-cyclohexylethyl), omega-chloroperfluorohexyl, 2-hydroperfluoropropyl, perfluoro(3-morpholinopropyl), and perfluoro(3-piperidinopropyl).

The combined electron withdrawing nature of the $SO_2R_f$ group and the X group is influential in providing the desired catalytic activity; the greater the electron withdrawing nature, the greater the catalytic activity will be of the fluoroaliphaticsulfonyl substituted ethylene compounds of the invention. The electron withdrawing nature of the $SO_2R_f$ and X groups can be determined by various known methods, e.g., by Hammett sigma (para) values as obtained by the method disclosed by H. H. Jaffe, Chem. Rev. 53 191 (1953). For the purpose of providing useful catalytic activity the combined electron withdrawing nature of the $SO_2R_f$ and X groups should provide a sigma (para) value of at least 1.0, with the X group having a sigma (para) value of at least 0.5. Preferably, the $SO_2R_f$ group has a sigma (para) value of at least 0.7, providing a combined sigma (para) value of at least 1.2 for the two groups. A benzoyl radical, for example, has a sigma (para) value of 0.5. A preferred $SO_2R_f$ group is $SO_2CF_3$ having a sigma (para) value of 0.9. A very useful fluoroaliphaticsulfonyl substituted ethylene is provided when both X and and $SO_2R_f$ are $SO_2CF_3$ groups. Additionally, exemplary organic radicals providing useful X groups include cyano, arylcarbonyl, alkylcarbonyl, perfluoroalkylcarbonyl, perfluoroalkylsulfonyl, nitro, fluorosulfonyl, and chlorosulfonyl groups.

The novel substituted ethylene compounds of the invention are most conveniently formed by condensation of precursor fluoroaliphaticsulfonyl methanes with aldehydes and N-formyl compounds in a chemical condensation reaction which can be illustrated as follows:

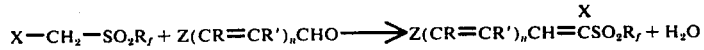

wherein X, $R_f$, Z, R and R' are as defined above. The reaction of the N-formyl compounds is usually in the presence of a carboxylic acid anhydride such as acetic anhydride and propionic anhydride.

In another method, the substituted ethylene compounds can be obtained by the reaction of an alkali metal salt of the fluoroaliphaticsulfonyl methane with the N-formyl compound in presence of an active acid halide which reaction can be illustrated as follows:

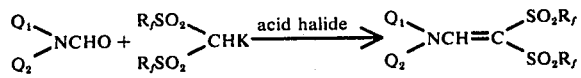

wherein $Q_1$ and $Q_2$ can be monovalent radicals such as hydrogen, alkyl, aryl, arylalkyl or (when taken together) a divalent radical such as $-(CH_2)_5-$ or $-CH_2CH_2OCH_2CH_2-$ to form a ring structure. The active acid halides useful in the process are those that form complex halides with the N-formyl compounds, such as are described, for example, by H. Eilingsfeld, et al, Angew, Chem., 72 836 (1960). Examples of active acid halides include benzoyl chloride, benzoyl bromide, acetyl chloride, phosphorus oxychloride, phosphorus trichloride, thionyl chloride and phosgene. In the reaction, an equimolar amount of the active acid chloride is usually used.

Yet another useful method of obtaining certain of the substituted ethylene compounds of the invention includes condensation of active hydrogen-containing substituted ethylene compounds (previously made according to the invention), e.g., $(CF_3SO_2)_2C=CHCH_2C_6H_5$, with additional aldehyde to provide substituted ethylene compounds having additional substituents.

Useful fluoroaliphatic sulfonyl methanes are preferably represented by the general formula $X-CH_2-SO_2R_f$ wherein $R_f$ and X are as described above. Certain known compounds will provide useful fluoroaliphatic methane precursors, e.g., see the aforementioned article by T. Gramstad and R. N. Haszeldine. Known compounds such as $CF_3SO_2CH_2SO_2CF_3$ and $CF_3SO_2CH_2SO_2C_6H_5$ provide useful examples.

It will be noted that the combined electron-withdrawing nature of the $SO_2R_f$ and the X groups will be sufficient to at least make one of the hydrogen atoms of the methylene group of the fluoroaliphaticsulfonyl methane precursor sufficiently acidic, i.e., having a pKa of less than 7, to permit the condensation reaction with an aldehyde or N-formyl compound to occur, and to provide compounds of the invention having catalytic utility.

Novel fluoroaliphaticsulfonyl methane precursors have been prepared and found useful in providing the novel substituted ethylenes of the invention on condensation with an aldehyde or an N-formyl compound. These precursors are preferably represented by the general formula:

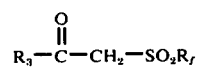

wherein $R_f$ is as described above and $R_3$ is alkyl, for example having 1 to 18 carbon atoms (preferably 1 to 8), a fluoroaliphatic group such as $R_f$ as defined above, or aryl such as a phenyl, naphthyl, biphenylyl, tolyl, or anisyl group.

The novel fluoroaliphaticsulfonyl methanes of the invention are conveniently prepared by reaction of a fluoroaliphaticsulfonyl methyl magnesium halide with a suitable acyl halide as is preferably represented by the following general formula:

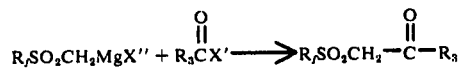

wherein X" is monovalent chlorine, bromine or iodine, X' is monovalent chlorine or fluorine, and $R_f$ and $R_3$ are as defined above.

The reaction for producing the novel fluoroaliphaticsulfonyl methanes is most conveniently carried out by mixing the acyl halide in an inert organic reaction medium such as tetrahydrofuran containing the fluoroaliphatic methyl magnesium halide under anhydrous conditions, acidifying the mixture, and removing the product from the organic reaction medium.

It should be noted that the novel fluoroaliphaticsulfonyl methanes, as well as providing precursors for the fluoroaliphatic substituted ethylenes of the invention, are themselves useful acidic catalysts for epoxy polymerization.

The aldehydes and N-formyl compounds useful in the condensation reaction to produce the novel fluoroaliphaticsulfonyl substituted ethylenes of the invention can be represented by the general formula $Z(CR=CR')_nCHO$ wherein R, R', Z, and n are as defined above. Exemplary useful aldehydes and N-formyl compounds include:

Aromatic aldehydes benzaldehyde
4-nitrobenzaldehyde
2-chlorobenzaldehyde
4-bromobenzaldehyde
4-cyanobenzaldehyde
4-hydroxybenzaldehyde
3,4-dichlorobenzaldehyde
2-hydroxybenzaldehyde
3,4-dihydroxybenzaldehyde
3-bromo-6-methoxybenzaldehyde
4-methoxybenzaldehyde
mesitaldehyde
4-hydroxy-3-ethoxybenzaldehyde
3-bromo-6-hydroxybenzaldehyde
2,3-dimethoxy-5-bromobenzaldehyde
2,5-dimethoxybenzaldehyde
2-isopropoxybenzaldehyde
2,4,5-trimethoxybenzaldehyde
4-valeryloxybenzaldehyde
3-methyl-4-benzyloxybenzaldehyde
3,5-di-t-butyl-4-hydroxybenzaldehyde
4-acetoxybenzaldehyde
4-acetamidobenzaldehyde
4-(methoxymethyl)benzaldehyde
3,4,5-triacetoxybenzaldehyde
2-benzaldehydesulfonic acid, sodium salt
4-methoxybenzaldehyde-3-sulfonic acid, sodium salt
4-fluorobenzaldehyde
3-trifluoromethylbenzaldehyde
4-formylphenoxyacetic acid, sodium salt
terephthalaldehyde
4-hydroxyisophthalaldehyde
4 methoxyisophthalaldehyde
2,5-dimethoxyterephthalaldehyde
1-naphthaldehyde
2-naphthaldehyde
azulene-1-carboxaldehyde
2-hydroxy-1-naphthaldehyde
ferrocene carboxaldehyde
5,6,7,8-tetrahydronaphthalene-2-carboxaldehyde
9-anthraldehyde
2,5-dibutoxyterephthalaldehyde
2,4-dimethyl-7-isopropylazulene-1-carboxaldehyde
tolualdehyde 4-(2'-chloroethylthio)benzaldehyde Heterocyclic aldehydes 2-furaldehyde
thiophene-2-carboxaldehyde
pyridine-2-carboxaldehyde
pyrrole-2-carboxaldehyde
β-(2-thienyl)acrolein
3,4-dimethylpyrrole-2-carboxaldehyde
4-carbethoxy-5-methyl-2-furaldehyde
4-carbethoxy-5-phenyl-2-furaldehyde
3,5-dimethyl-4-acetylpyrrole-2-carboxaldehyde Arylalkyl or arylalkenyl aldehydes phenylacetaldehyde
cinnamaldehyde
11-phenylundecapentaenal Acyclic aldehydes crotonaldehyde
acrolein
acetaldehyde
n-butyraldehyde N-formyl compounds formamide
N-benzylformamide
N-(p-methoxy benzyl)formamide
N-triphenylmethylformamide
4-formylaminotoluene
1-formylaminonaphththalene
5-formylaminocaproamide
N-formylmorpholine
dimethyl formamide
formanilide A list of other useful aldehydes can be found in Chap. 2, *Organic Reactions*, Vol. 15, (1967) edited by A. C. Cope, New York.

One convenient method for preparing the fluoroaliphaticsulfonyl substituted ethylene compounds of this invention consists in bringing a fluoroaliphaticsulfonyl methane precursor into intimate contact with an aldehyde in a liquid reaction medium, which is non-reactive to the reactants and the product, at a suitable temperature which is generally in the range of 60° to 150°C., and maintaining the mixture at the temperature until the reaction is essentially complete. The liquid reaction medium is preferably a solvent for the reactants and the product; most preferably it will also form an azeotrope with water that is a reaction byproduct, giving a convenient means of removing the water from the reaction mixture. Examples of suitable reaction media include benzene, toluene, xylene, mesitylene, and chloroform. Anhydrous basic tertiary amines such as pyridine can also be used as a reaction medium although they usually produce low yields of the condensation product —especially with bis(fluoroaliphaticsulfonyl)methanes. Strongly basic solutions such as aqueous sodium hydroxide or sodium methoxide are to be avoided because they may degrade the condensation product. Upon completion of the reaction (which is evidenced by cessation of the production of water), the condensation product is separated from the reaction mixture, e.g., by distillation or evaporation of reaction medium, with further purification, if desired, by re-crystallization from liquid anhydrous media.

The preferred reaction temperature range is from about 60° to about 150°C. but temperatures as low as 25° and as high as 165°C. or even higher can be used.

The reaction, to proceed satisfactorily, may require the presence of a catalytic amount of organic base such as piperidine, triethylamine, or the organic acid salt of piperidine or triethylamine. Use of a catalyst, however, is not required where the precursor fluoroaliphaticsulfonyl methane is a bis(perfluoroaliphaticsulfonyl) methane.

For convenience, the reactions of this invention are conducted at normal atmospheric pressure but pressures above and below atmospheric pressure can be used. The reactor can be a vessel of simple design constructed of any non-reactive materials such as glass, ceramic ware, or stainless steel and is preferably provided with means for agitation, cooling and heating, and equipped to protect the charge from atmospheric contaminants.

The molar ratio of the precursor fluoroaliphaticsulfonyl methane to the aldehyde used in the method may be varied, but best results are obtained when equimolar amounts of aldehyde and fluoroaliphaticsulfonyl methane are used. With aliphatic aldehydes such as acetaldehyde, however, a molar ratio of 2:1 or greater (aldehyde to methane) is preferred.

The particular amount of fluoroaliphaticsulfonyl ethylene catalyst to be used and the temperature of polymerization are dependent on the particular monomers and catalyst used, as well as the particular application to be made. Generally, the amount of fluoroaliphaticsulfonyl substituted ethylene catalyst to be used will be in the range of 0.1 to 20 weight percent, preferably 0.1 to 5 weight percent based on the weight of monomeric material. The temperature will generally be 25°–150°C. or higher.

The vinyl monomers polymerized by fluoroaliphaticsulfonyl substituted ethylenes of the invention contain a vinyl group and are typified by vinyl alkyl ethers, such as vinyl methyl ether, vinyl ethyl ether, vinyl n-butyl ether, vinyl 2-chloroethyl ether, vinyl isobutyl ether, vinyl phenyl ether and vinyl 2-ethylhexyl ether, vinyl ethers of substituted aliphatic alcohols, such as ω-hydroxybutyl vinyl ether, and N-vinyl compounds such as N-vinyl-N-methyl octanesulfonamide. A description of vinyl monomers and their use in preparing polymers is set forth in "Vinyl and Related Polymers", by Schildknecht, published by John Wiley & Sons, Inc., New York (1952).

The epoxide monomers polymerized by the fluoroaliphaticsulfonyl substituted ethylenes of the invention include both monomeric and polymeric aliphatic, cycloaliphatic, aromatic or heterocyclic epoxy compounds typically having an epoxy equivalency (i.e., the number of epoxy groups contained in the average molecule) of from 1.0 to 6.0, preferably 1 to 3, this value being the average molecular weight of the epoxide divided by the epoxide equivalent weight. The epoxide monomers are well known and include such epoxides as epihalohydrins, e.g., epichlorohydrin, alkylene oxides, e.g., propylene oxide, styrene oxide, alkenyl oxides, e.g., butadiene oxide, glycidyl esters, e.g., glycidyl acetate, glycidyl-type epoxy resins, e.g., the diglycidyl ethers of Bisphenol A and of novolak resins, such as described in "Handbook of Epoxy Resins", by Lee and Neville, McGraw-Hill Book Co., New York (1967).

Particularly useful epoxides which can be used in this invention are those which contain one or more cyclohexane oxide groups such as the epoxycyclohexanecarboxylates, typified by 3,4-epoxycyclohexylmethyl-3,4-epoxycyclohexanecarboxylate, 3,4-epoxy-2-methylcyclohexane carboxylate, and bis(3,4-epoxy-6-methylcyclohexylmethyl)adipate. For a more detailed list of useful epoxides of this nature, reference is made to the U.S. Pat. No. 3,117,099.

Further epoxides which are particularly useful in the practice of this invention include glycidyl ether monomers of the formula

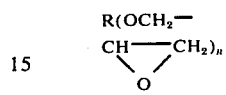

where R is alkyl or aryl and $n$ is an integer of 1 to 6. An example is the glycidyl ethers of polyhydric phenols obtained by reacting a polyhydric phenol with an excess of chlorohydrin, such as epichlorohydrin, e.g., the diglycidyl ether of bisphenol A. Further examples of epoxides of this type which can be used in the practice of this invention are described in U.S. Pat. No. 3,018,262.

In particular, epoxides which are readily available include propylene oxide, epichlorohydrin, styrene oxide, vinyl cyclohexane oxide, glycidol, glycidyl methacrylate, diglycidyl ether of bisphenol A (e.g., Epon 828 and DER 332), vinylcyclohexene dioxide (e.g., ERL-4206), 3,4-epoxycyclohexylmethyl-3,4-epoxycyclohexane carboxylate (e.g., ERL 4221), 3,4-epoxy-6-methycyclohexylmethyl-3,4-epoxy-6-methylcyclohexane carboxylate (e.g., ERL-4201), bis(3,4-epoxy-6-methylcyclohexylmethyl)adipate (e.g., ERL 4289), bis(2,3-epoxycyclopentyl)ether (e.g., ERLA-0400), aliphatic epoxy modified with polypropylene glycol (e.g., ERL-4050 and ERL-4052), dipentene dioxide (e.g., ERL-4269), epoxidized polybutadiene (e.g., Oxiron 2001), 1,4-butanediol diglycidyl ether (e.g., Araldite RD-2), polyglycidyl ether of phenolformaldehyde novolak (e.g., DEN-431 and DEN-438) and resorcinol diglycidyl ether (e.g., Kopoxite).

EXAMPLES

This invention is further illustrated by the following examples wherein all parts are given by weight and temperatures are in degrees centigrade unless otherwise specified.

EXAMPLE 1

Catalyst Preparation

A mixture of 7.5 g. (0.05 mole) of 1-naphthaldehyde, 14.0 g. (0.05 mole) of bis(perfluoromethylsulfonyl)methane and 50 ml. of benzene was heated under reflux (4 hrs.) until water ceased to be formed. During reaction, the water was removed by distillation using a Barrett-type water-receiver. The mixture was heated under reduced pressure (0.02 mm) to 100°C. leaving a residue which was recrystallized from hexane to yield 12.7 g. of the fluoroaliphaticsulfonyl substituted ethylene compound, 1,1-bis(perfluoromethylsulfonyl)-2-(1'-naphthyl)ethylene, having a melting point of 91°–93°, and a chemical structure as follows:

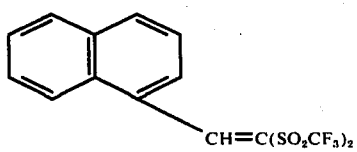

CH=C(SO₂CF₃)₂

Epoxide Polymerization

A solution of 0.03 g. of the 1,1-bis(perfluoromethylsulfonyl)-2-(1'-naphthyl)ethylene prepared above in 0.3 ml. of methylene chloride was added with stirring to 3.5 g. of 3,4-epoxycyclohexylmethyl-3,4-epoxycyclohexane carboxylate containing 0.1% of H₂O. The mixture was exposed to air for 15 min. and then heated at 75° for 5 min. giving a hard cured polymer.

EXAMPLE 2

A mixture of 8.0 g. (0.08 mole) of benzaldehyde, 14.0 g. (0.05 mole) of bis(perfluoromethylsulfonyl)methane, 0.1 g. of piperidine and 50 ml. of benzene was refluxed until production of water ceased. Benzene, water and starting material were removed by heating, giving 15 g. of a solid residue. Recrystallization of the solid residue from hexane gave 13.3 g. of β,β-bis(perfluoromethylsulfonyl) styrene, (CF₃SO₂)₂C=CHC₆H₅, m.p. 39°–41°.

EXAMPLE 3

A 250 ml. dry flask fitted with a stirrer, addition funnel and condenser connected to a drying tube was charged with 28 g. (0.1 mole) of bis(perfluoromethylsulfonyl)methane and 75 ml. of dry tetrahydrofuran. To the stirred solution was added 58 ml. of 3.0 molar methylmagnesium chloride in tetrahydrofuran. The mixture was stirred at room temperature for 0.5 hrs. and 15.0 g. (0.15 mole) of benzaldehyde added. The resultant mixture was stirred at room temperature for 3.5 hrs. and hydrolyzed by the slow addition of 80 ml. of 3N HCl. The organic phase was separated and heated to remove tetrahydrofuran and the residue extracted with diethyl ether. The extract was dried over magnexium sulfate and distilled to yield 13.3 g. of (CF₃SO₂)₂ C=CHC₆H₅, b.p. 103°–104° (0.05 mm.), which solidified on standing.

Polymerization of vinylcyclohexene dioxide to a solid cured product was effected at room temperature using about 1% by weight of the above benzaldehyde condensation product dissolved in methylene chloride.

EXAMPLE 4

A mixture of 10.0 g. (0.08 mole) of phenylacetaldehyde, 28.0 g. (0.1 mole) of bis(perfluoromethylsulfonyl)methane and 80 ml. of benzene was stirred under reflux and water (1.3 ml.) continuously removed. The reaction yielded 12.5 g. of 1,1-bis(perfluoromethylsulfonyl)-3-phenylpropene, (CF₃SO₂)₂C=CHCH₂C₆H₅, b.p. 112° (0.01 mm.).

EXAMPLE 5

A mixture of 4.8 g. (0.05 mole) of 2-furaldehyde, 14.0 g. (0.05 mole) of bis(perfluoromethylsulfonyl)methane and 50 ml. of benzene was stirred under reflux and water continuously removed. The reaction yielded 11.8 g. of 1,1-bis(perfluoromethylsulfonyl)-2-(2'-furyl)ethylene, (CF₃SO₂)₂C=CHC=CHCH=CHO, b.p. 109°–110° (0.01 mm). The condensation product was crystallized from hexane, giving a product having a m.p. of 78°–79°.

EXAMPLE 6

Using procedures described in Example 2, β,β-bis(perfluoromethylsulfonyl)-o-chlorostyrene, b.p. 117° at 1 mm., was prepared by condensation of O-chlorobenzaldehyde and bis(perfluoromethylsulfonyl)methane.

EXAMPLE 7

Using procedures described in Example 2, β,β-bis(perfluoromethylsulfonyl)-p-nitrostyrene, m.p. 102°–104°, was prepared by condensation of p-nitrobenzaldehyde with bis(perfluoromethylsulfonyl)methane.

EXAMPLE 8

Using procedures described in Example 1, β,β-bis(perfluoromethylsulfonyl)-3-ethoxy-4-hydroxystyrene, m.p. 82°–84°, was prepared by condensation of 3-ethoxy-4-hydroxybenzaldehyde with bis(perfluoromethylsulfonyl)methane. The compound was recrystallized from hexane.

EXAMPLE 9

A mixture of 5.0 g. (0.005 mole) of (C₈F₁₇SO₂)₂CH₂, 1.6 g. (0.01 mole) of 1-naphthaldehyde and 100 ml. of mesitylene was heated under reflux for 9 hrs. until water ceased to be produced. The mixture was allowed to cool and then filtered giving 5.1 g. of crude product. Recrystallization of the crude product from hexane gave 2.6 g. of the following product. m.p. 113°–114°.

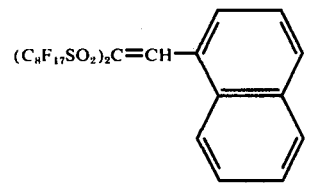

(C₈F₁₇SO₂)₂C=CH—

Anal. Calcd: C,30.1; F,57.8; H,0.7 Found: C,30.1; F,57.0; H,0.8.

EXAMPLE 10

A mixture of 14 g. (0.05 mole) of bis(perfluoromethylsulfonyl)methane, 6.6 g. (0.05 mole) of cinnamaldehyde and 50 ml. of benzene was heated under reflux until evolution of water ceased. There was obtained about 7.3 g. of

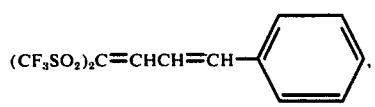

(CF₃SO₂)₂C=CHCH=CH— m.p. 93°–94°C.

EXAMPLE 11

Using the procedure described in Example 10, the reaction of bis(perfluoromethylsulfonyl)methane and pyrrole-2-carboxaldehyde gave $(CF_3SO_2)_2C=CH-\underset{\underset{H}{|}}{\boxed{\phantom{N}N\phantom{N}}}$, m.p. 112°–114°C.

EXAMPLE 12

Crotonaldehyde (3.5 g.; 0.05 mole) was added to 14 g. (0.05 mole) of bis(perfluoromethylsulfonyl)methane dissolved in 50 ml. of benzene. The mixture was heated under reflux until water evolution ceased. The reaction yielded $(CF_3SO_2)_2C=CHCH=CHCH_3$, b.p. 78° (0.2 mm.) and a higher boiling sulfone product having 31.7% fluorine and a molecular weight of about 1120.

EXAMPLE 13

Acetaldehyde (9.3 g.; 0.21 mole) in 20 mol. of benzene was added to 28 g. (0.1 mole) of bis(perfluoromethylsulfonyl)methane in 50 ml. of benzene. The mixture was stirred at room temperature for one hour and heated then under reflux until evolution of water ceased. The reaction yielded 8 g. of $(CF_3SO_2)_2C=CHCH=CHCH_3$, b.p. 108°–112° (2 mm.).

EXAMPLE 14

The reagent $CF_3SO_2CH_2MgCl$ was prepared from 22.0 g. (0.15 mole) of methyl perfluoromethylsulfone and 0.2 mole of methylmagnesium chloride in tetrahydrofuran. Butyryl chloride (30.0 g.; 0.3 mole) was added at room temperature and the mixture stirred for 2 hours. The mixture was hydrolyzed with 3 N HCl, the tetrahydrofuran phase separated and heated to remove solvent. The residue was dissolved in diethyl ether and the solution (dried over $MgSO_4$) heated to remove the ether, giving 14 g. of the novel fluoroalkylsulfonyl methane precursor, $CF_3SO_2CH_2COC_3H_7$ b.p. 90°C. (5 mm.). A sample was recrystallized from water, m.p. 67.5°–68.5°C.

Anal. Calcd: C, 33.0; F, 26.1; H, 4.1. Found: C, 33.1; F, 25.8; H, 4.5.

EXAMPLE 15

Using procedures described in Example 14, the novel fluoroalkylsulfonyl methane precursor, $C_4F_9SO_2CH_2COC_6H_5$, was prepared from methyl perfluorobutyl sulfone and benzoyl chloride. The compound melted at 73°–75°C.

EXAMPLE 16

Using procedures described in Example 14, 22.0 g. (0.15 mole) of methyl perfluoromethylsulfone was converted to $CF_3SO_2CH_2MgX$ and to this was added perfluoroacetyl chloride (0.22 mole), giving 20.7 g. liquid, b.p. 85°–88° (150 mm.) which contained the novel fluoroalkylsulfonyl methane precursor $CF_3SO_2CH_2COCF_3$, and its enol isomer.

EXAMPLE 17

Dimethylformamide (23.4 g; 0.32 mole) was slowly added to a stirred mixture of 100 g (0.32 mole) of $(CF_3SO_2)_2CHK$, 48 g. (0.34 mole) of benzoyl chloride and 350 ml. of carbon tetrachloride under nitrogen (slight exotherm). The mixture was stirred at room temperature for 1 hour and then at 60°C. for 1 hour. After addition of 250 ml. of carbon tetrachloride, filtration yielded about 135 g. of crude product containing potassium chloride. Recrystallization from toluene gave 75 g. of 1,1-bis(perfluoromethylsulfonyl)-2-dimethylaminoethylene, $(CF_3SO_2)_2C=CHN(CH_3)_2$, m.p. 116°–118°C.

Anal. Calcd: C, 21.3; F, 34.0; N, 4.2. Found: C, 21.4; F, 34.3; F, 4.1.

A mixture of 3,4-epoxycyclohexylmethyl-3,4-epoxycyclohexane carboxylate and the above product (2% by weight) was heated at 150°C. for 15 hours giving a hard polymer.

EXAMPLE 18

Formamide (2.8 g.; 0.06 mole) was slowly added to a stirred mixture of 20.0 g. (0.06 mole) of $(CF_3SO_2)_2CHK$, 9.8 g. (0.07 mole) of benzoyl chloride under nitrogen (slight exotherm) and 75 ml. of carbon tetrachloride. The mixture was heated under reflux for 1.5 hours. Filtration gave 20.7 g. of crude product which was slurried with diethyl ether to remove KCl, leaving about 19 g. of ether soluble $(CF_3SO_2)_2C=CHNH_2$ (m.p., 121°–122° from chloroform).

Anal. Calcd: C, 15.6; F, 37.1; H, 1.0. Found: C, 15.8; F, 37.2; H, 1.2.

EXAMPLE 19

Using procedures found in Example 17, the reaction of N-formylmorpholine with the potassium salt of bis(-perfluoromethylsulfonyl)methane gave $(CF_3SO_2)_2C=CHN\underset{\phantom{x}}{\boxed{\phantom{xxx}O\phantom{xxx}}}$, m.p. 110°–112.5° (toluene).

The reaction of bis(perfluoromethylsulfonyl)methane and N-formyl compounds was also carried out using solvents such as acetic anhydride, but the yields of the product were lower.

EXAMPLES 20–28

The following compounds are further Examples prepared by the above-described procedures:

$CH_3CH=C(CH_3)CH=C(SO_2CF_3)_2$ $C_6H_5CH=C(CH_3)CH=C(SO_2CF_3)_2$ $\boxed{O}\!-\!CH=CH-CH=C(SO_2CF_3)_2$ $CH_3C(CH_3)=CHCH_2CH_2C(CH_3)=CHCH=C(SO_2CF_3)_2$ $(C_6H_5)_2C=CHCH=C(SO_2CF_3)_2$ $C_6H_5CH=\underset{\underset{O=C-C_6H_5}{|}}{C}SO_2CF_3$ $C_6H_5CH=\underset{\underset{O=C-CF_3}{|}}{C}SO_2CF_3$

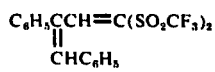

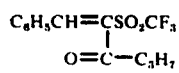

What is claimed is:

1. A fluoroaliphaticsulfonyl ethylene compound especially suited as a catalyst in epoxide, vinyl ether, and N-vinyl monomer polymerization and having the formula

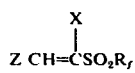

wherein $R_f$ is a monovalent saturated fluoroaliphatic radical; X is a monovalent, non-ionic, electron withdrawing radical at least as electron withdrawing as a benzoyl radical; Z is amino, dialkylamino, arylalkylamino, diarylamino, alkylamino, or arylamino.

2. The compound of claim 1 wherein X is $SO_2R'_f$ wherein $R'_f$ is a monovalent saturated fluoroaliphatic radical.

3. A process comprising contacting monomer selected from the group consisting of epoxides, vinyl ethers, and N-vinyl compounds with a catalytic amount of the compound of claim 1 to effect polymerization of said monomer.

4. 1,1-bis(perfluoromethylsulfonyl)-2-dimethylamino ethylene.

5. A fluoroaliphaticsulfonyl ethylene compound especially suited as a catalyst in epoxide, vinyl ether, and N-vinyl monomer polymerization and having the formula

wherein $R_f$ is a monovalent saturated fluoroaliphatic radical; X is a monovalent, non-ionic, electron withdrawing radical at least as electron withdrawing as a benzoyl radical, and Z is amino, dialkylamino, or alkylamino.

6. The compound of claim 5 wherein X is $SO_2R'_f$ wherein $R'_f$ is a monovalent saturated fluoroaliphatic radical.

7. The compound of claim 6 wherein $R'_f$ and $R_f$ are perfluoroaliphatic radicals having 1 to 18 carbon atoms.

8. The compound of claim 7 wherein $R'_f$ and $R_f$ are perfluoromethyl groups.

9. A process comprising contacting monomers selected from the group consisting of epoxides, vinyl ethers, and N-vinyl compounds with a catalytic amount of the compound of claim 5 to effect polymerization of said monomer.

* * * * *